United States Patent
Schmidt et al.

(10) Patent No.: US 10,231,787 B2
(45) Date of Patent: Mar. 19, 2019

(54) METHOD AND SYSTEM FOR MEDICAL TRACKING USING A PLURALITY OF CAMERA POSITIONS

(75) Inventors: Robert Schmidt, Neubiberg (DE); Johannes Manus, Munich (DE); Fritz Vollmer, Munich (DE)

(73) Assignee: Brainlab AG, Munich (DE)

( * ) Notice: Subject to any disclaimer, the term of this patent is extended or adjusted under 35 U.S.C. 154(b) by 789 days.

(21) Appl. No.: 14/367,475

(22) PCT Filed: Jan. 12, 2012

(86) PCT No.: PCT/EP2012/050398
§ 371 (c)(1),
(2), (4) Date: Jun. 20, 2014

(87) PCT Pub. No.: WO2013/104420
PCT Pub. Date: Jul. 18, 2013

(65) Prior Publication Data
US 2015/0332465 A1   Nov. 19, 2015

(51) Int. Cl.
*A61B 34/20* (2016.01)
*H04N 5/232* (2006.01)
(Continued)

(52) U.S. Cl.
CPC ............ *A61B 34/20* (2016.02); *A61B 90/361* (2016.02); *G01S 5/02* (2013.01); *G01S 5/0247* (2013.01);
(Continued)

(58) Field of Classification Search
CPC ............ A61B 34/20; A61B 2034/2046; H04N 5/23296; H04N 5/23299
See application file for complete search history.

(56) References Cited

U.S. PATENT DOCUMENTS

2005/0145257 A1* 7/2005 Barrera ............ G06Q 10/06316
128/898
2005/0281385 A1* 12/2005 Johnson .................. A61B 6/12
378/163

(Continued)

FOREIGN PATENT DOCUMENTS

DE   10 2008 055 918 A1   5/2010
WO   2005/076033            8/2005

OTHER PUBLICATIONS

WIPO, International Preliminary Report on Patentabilty for PCT/EP2012/050398 (dated Jul. 15, 2014).*

(Continued)

*Primary Examiner* — David N Werner
(74) *Attorney, Agent, or Firm* — Tucker Ellis LLP (57) ABSTRACT

A method for tracking trackable objects using a medical tracking device, the tracking device being a camera or an EM transmitter, during a medical workflow comprising a plurality of workflow steps, wherein each trackable object has at least one marker and the method comprises the steps of: —acquiring a set of camera positions, wherein each tracking device position is associated with at least one workflow step; —identifying a workflow; —sequentially and automatically moving the tracking device to the camera positions associated with the workflow steps; and—performing a tracking step only when the tracking device is in a fixed position.

18 Claims, 3 Drawing Sheets

(51) Int. Cl.
*A61B 90/00* (2016.01)
*G01S 5/02* (2010.01)
*G01S 5/16* (2006.01)
*G06T 7/73* (2017.01)
*A61B 34/00* (2016.01)
*A61B 34/30* (2016.01)

(52) U.S. Cl.
CPC .............. *G01S 5/16* (2013.01); *G01S 5/163* (2013.01); *H04N 5/23296* (2013.01); *H04N 5/23299* (2018.08); *A61B 34/30* (2016.02); *A61B 2034/2051* (2016.02); *A61B 2034/2057* (2016.02); *A61B 2034/254* (2016.02); *F04C 2270/041* (2013.01); *G06T 7/73* (2017.01); *G06T 2207/10028* (2013.01); *G06T 2207/30004* (2013.01); *G06T 2207/30204* (2013.01); *G06T 2207/30244* (2013.01)

(56) References Cited

U.S. PATENT DOCUMENTS

| | | | |
|---|---|---|---|
| 2006/0071135 A1 | 4/2006 | Trovato | |
| 2007/0014567 A1 | 1/2007 | Rossner et al. | |
| 2007/0078678 A1* | 4/2007 | DiSilvestro | G06F 19/00 705/2 |
| 2009/0192384 A1* | 7/2009 | Fontius | A61B 5/0555 600/425 |
| 2011/0029913 A1* | 2/2011 | Boillot | G06F 3/011 715/776 |
| 2011/0196377 A1* | 8/2011 | Hodorek | A61B 17/155 606/87 |
| 2011/0251625 A1 | 10/2011 | Bulitta et al. | |
| 2012/0307027 A1* | 12/2012 | Popovic | B25J 9/1697 348/65 |
| 2014/0253712 A1* | 9/2014 | Vilsmeier | H04N 7/183 348/77 |

OTHER PUBLICATIONS

EPO, Machine Translation of WO/2005/076033.*
English-Language Translation of WO 2005076033 A1 (prepared by USPTO translator) (Year: 2017).*
A. Pandy, A.L. Reisner, B. King, N. Lucas, A. Composto, M. Klein, & R.D. Ellis, "A Review of Camera Viewpoint Automation in Robotic and Laparoscopic Surgery", 3 Robotics 310-329 (Aug. 14, 2014) (Year: 2014).*
A. James, D. Vieraia, B. Lo, A. Darzi, & G.G. Yang, "Eye-Gaze Driven Surgical Workflow Intervention", 4792 Lecture Notes in Comp. Sci. 110-118 (Nov. 2007) (Year: 2007).*
N. Navab, T. Blum, L. Wang, A. Okur, & T. Wendler, "First Deployments of Augmented Reality in Operating Rooms", 45.7 Computer 48-55 (Jul. 2012) (Year: 2012).*
N. Padoy, "Workflow and Activity Modeling for Monitoring Surgical Procedures", Universite Henri Poincare (2010) (Year: 2010).*
O. Weede, F. Dittrich, H. Woern, B. Jensen, A. Knoll, D. Wilhelm, M. Kranzfelder, A. Schneider, & H. Feussner, "Workflow Analysis and Surgical Phase Recognition in Minimally Invasive Surgery", Proc. of the 2012 IEEE Int'l Conf. on Robotics & Biomimetics (Dec. 2012) (Year: 2012).*
S.Y. Ko, J. Kim, W.J. Lee, & D.S. Kwon, "Surgery Task Model for Intelligent Interaction between Surgeon and Laparoscopic Assistant Robot", 8 J. of Robotics & Mechatronics 38-46 (Jan. 2007) (Year: 2007).*
European Patent Office, Written Opinion and International Search Report for corresponding PCT/EP2012/050398, pp. 1-7, dated Oct. 24, 2012.

* cited by examiner

METHOD AND SYSTEM FOR MEDICAL TRACKING USING A PLURALITY OF CAMERA POSITIONS

This application is a national phase application of International Application No. PCT/EP2012/050398 filed Jan. 12, 2012 and published in the English language.

The present invention relates to a method and a system for medically tracking trackable objects using a tracking device during a medical workflow comprising a plurality of workflow steps. Each trackable object has at least one marker.

In known medical tracking systems, a tracking camera, in particular a 3D tracking camera, observes a certain spatial region in order to detect markers. However, markers cannot be detected if the line of sight between the camera and the marker is obstructed. In document DE 10 2008 055 918 A1, the tracking camera is moved during the tracking process in order to avoid an obstruction in the field of view. However, the tracking accuracy is reduced while the tracking camera is moving. The problem equally arises for medical tracking systems in which an EM transmitter transmits an EM signal (electromagnetic signal) which is received by a marker, while the received signal is analysed in order to determine the position of the marker.

This problem is solved by the subject-matter of any of the appended independent claims. Advantages, advantageous features, advantageous embodiments and advantageous aspects of the present invention are disclosed in the following and contained in the subject-matter of the dependent claims. Different advantageous features can be combined in accordance with the invention where technically expedient and feasible. In particular, a feature of one embodiment which has the same or a similar function as another feature of another embodiment can be exchanged. In particular, a feature of one embodiment which adds an additional function to another embodiment can be added to said other embodiment.

The present invention relates to a method for tracking trackable objects using a tracking device during a medical workflow comprising a plurality of workflow steps, wherein each trackable object has at least one marker. One step of the method involves acquiring a set of tracking device positions, wherein each tracking device position is associated with at least one workflow step. Another step involves identifying a workflow. Yet another step involves sequentially and automatically moving the tracking device to the tracking device positions associated with the workflow steps. According to the present invention, the actual tracking step is performed only when the tracking device is in a fixed position, i.e. when the camera is not moving.

The tracking device can be a tracking camera or an EM transmitter. EM tracking systems using an EM transmitter and one or more EM receivers acting as markers on objects are widely known, such that a detailed description is omitted. The EM transmitter can be at least one antenna or a combination of at least one antenna with transmitter electronics. In the following, the tracking device is always described as being a camera and the tracking device position is referred to as camera position. However, the invention is further equally applicable to a tracking device being an EM transmitter, such that the camera position corresponds to an EM transmitter position. The tracking volume of a tracking camera typically is the field of view of the camera, while the tracking volume of an EM transmitter typically is a spatial region which is permeated by the EM field generated by the EM transmitter.

Within the present invention, the tracking camera can assume several camera positions, and a camera position to be assumed is defined for a particular workflow step. The camera position assigned to a particular step of the medical workflow is preferably an optimum position regarding the accuracy with which the objects used during this workflow step are tracked. The set of camera positions preferably comprises two or more, three or more or five or more camera positions. In other words, the camera assumes two or more, three or more or five or more camera positions during the workflow.

Automatically moving the camera means that no physical manipulation of the camera by a human being is required in order to move the camera into a particular position. The camera can for example be a motorised camera. In this document, the term "position" means the spatial location in up to three translational dimensions and/or the alignment in up to three rotational dimensions.

Performing the tracking step only when the camera is in a fixed position means that any inaccuracies in the tracking result introduced by the movement of the camera during the tracking process are eliminated, while the camera can still be positioned for each workflow step in order to achieve a sufficient tracking result.

It is the function of a marker to be detected by a marker detection device (for example, a camera or an ultrasound receiver), such that its spatial position (i.e. its spatial location and/or alignment) can be ascertained. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A marker device can for example be a reference star or one or more (individual) markers in a predetermined spatial relationship. A marker device comprises one, two, three or more markers in a predetermined spatial relationship. This predetermined spatial relationship is in particular known to a navigation system and for example stored in a computer of the navigation system.

The expression "acquiring" data, such as the set of camera positions, encompasses in particular (within the framework of a data processing method) the scenario in which the data are determined by the data processing method or program. The meaning of acquiring data in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. Acquiring data can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can be made "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, acquiring data can also involve commanding a device to obtain and/or provide the data to be acquired.

The camera position is preferably verified, for example after the camera position has been changed or before the first workflow step is performed. This verification can be based on at least one marker which is in a fixed position, for example attached to an item of operating room infrastructure such as an operating room table. If the camera position is to be verified after it has been changed, it can be verified relative to at least one marker or a marker device which has not changed its position during the movement of the camera. The change in the position of the camera can be calculated from the relative positions of the camera and the at least one marker or the marker device for two different camera positions.

There are numerous ways of determining a camera position within the set of camera positions. One option is to manually enter a position into the set of camera positions. Among other implementations, the up to six dimensions of the position can be entered manually, for example as coordinates and/or angles, for example as numerical values. Another option would be to position the camera by controlling the camera position using an input device, such as a keyboard, a joystick, a mouse, a touch screen or any other suitable device, and then using the current position of the camera as a position in the set of camera positions.

Another option is to determine a position to be included the set of camera positions automatically. This preferably includes the steps of: sequentially moving the camera to a plurality of test positions, either automatically or manually; storing a test position as a candidate position if all the markers of all the trackable objects used within a particular workflow step are within the tracking volume of the camera; and selecting the candidate position in which the distances from the markers to the centre of the tracking volume are minimised as a position to be included in the set of camera positions. This utilises the fact that the tracking accuracy of markers in a central portion of the tracking volume is typically higher than the tracking accuracy of markers in a peripheral portion of the tracking volume.

The criterion of the minimised distance can be implemented in a number of ways. Example options include minimising the average distance or minimising the weighted average distance.

As an alternative to or in addition to the criterion of minimising the distance from the markers to the centre of the tracking volume, it is also possible to use the criterion of selecting the highest possible candidate position. If, for example, several candidate positions result in the same minimum distance, then the candidate position with the highest possible position is selected. A high position of the tracking camera reduces the probability of an obstacle obstructing the line of sight between the camera and a marker.

Another option is to select the candidate position in which the angles between the line of sight of the camera and normal vectors which are normal to a plane in which the markers of a trackable object lie are minimised. This utilises the fact that the tracking accuracy for an object is at its highest if the markers do not overlap in the outputted images of the tracking camera.

In another embodiment, a test position is stored as a candidate position if all the markers of all the trackable objects used within a particular workflow step are within a predetermined sub-volume of the tracking volume. This sub-volume is preferably a central portion of the tracking volume, in which the tracking accuracy is at its highest. Within this embodiment, the number of candidate positions is reduced, such that fewer candidate positions have to be analysed in order to find the position which is to be stored as a position within the set of camera positions.

In yet another embodiment, priorities are assigned to the trackable objects used within a particular workflow step, and a test position is stored as a candidate position if all the markers of objects with a priority which is higher than a threshold value are within a predetermined sub-volume of the tracking volume. This embodiment ensures that at least the objects with a priority which is higher than the threshold value can be tracked to a desired level of accuracy. This is particularly useful if there is no test position of the tracking camera in which all the markers of all the objects to be tracked lie within the sub-volume of the tracking volume.

Additionally or alternatively, priorities assigned to the trackable objects are used to select one of the candidate positions for inclusion in the set of camera positions.

According to another embodiment, a set of candidate positions is stored for each of a plurality of workflow steps, and the number of (preferably consecutive) workflow steps which comprise the same candidate position in their respective sets of candidate positions is determined. The candidate position which features the highest number of times in the workflow steps is selected as a position to be included in the set of camera positions. This approach reduces the number of times the camera has to be repositioned, at the possible expense that the camera position might not be the best possible camera position for a particular workflow step.

In another embodiment, the method comprises the additional step of providing indication information which indicates that no suitable camera position has been found and that the camera should be repositioned. The indication information is preferably represented by an indication information signal, which can be optical, acoustic and/or tactile in nature. Repositioning the camera means that a base, such as a tripod, relative to which the camera position can be selected, is changed, for example by moving the base to another position. This new position of the camera base enables camera positions other than those of the previous camera base position, such that a test position may then be found in which all the criteria for using this test position in the set of camera positions are fulfilled. In another case, the location of the camera is fixed and only the orientation of the camera is adjustable. In this case, the camera has to be relocated.

In one embodiment, the medical workflow is identified manually by inputting identification data which identify a workflow, for example by selecting the medical workflow from a list of medical workflows. However, the medical workflow is preferably identified automatically. The medical workflow is for example identified by identifying trackable objects. This can mean identifying the type of an object or identifying a unique object. Since every medical workflow requires a particular set of objects, the medical workflow can be determined from the objects present.

Upon identifying trackable objects, the camera preferably assumes a plurality of positions to enhance its detection volume, wherein the detection volume is a spatial region in which markers can be detected for the current camera position. In particular, the camera positions are chosen such that the detection volumes for these camera positions (slightly) overlap. The enhanced detection volume preferably comprises the whole operation room environment. In one embodiment, the camera has a restricted range of motion limiting possible camera positions. At least some of the camera positions are preferably on the border of this range of motion.

An object is preferably identified using the tracking camera, for example by identifying the shape of an object using image processing or by determining the configuration of markers connected to an object. Additionally or alternatively, objects are identified using RFID chips attached to them.

A trackable object can be an anatomical structure, such as a bone or a part of a bone, or a medical instrument, such as a scalpel, a cutting block, a clamp, a treatment beam generator, a C-arm, an ultrasound transducer or an imaging device such as an x-ray, CT or MRT device.

In one embodiment, a camera position is corrected on the basis of the position of a marker attached to a body or to a part of a body to be treated. The marker, which can also be a plurality of markers, thus acts as a reference. Within this embodiment, the camera position can be adjusted if the body is in a position which differs from an (expected) position on which the camera position within the set of camera positions is based. The motivation for this embodiment is that the trackable objects are typically in positions relative to the body, and not necessarily relative to a reference system in which the camera positions within the set of camera positions are typically defined. Alternatively, the camera positions within the set of camera positions are defined relative to the reference.

In another embodiment, the tracking device position is corrected on the basis of the detectability of the markers. In the case of a camera, the camera position is corrected on the basis of the visibility of the markers. This means that the camera is first moved into the position specified in the set of camera positions and the visibility of the markers is then determined. If the required markers are not all visible, then the camera position is (preferably automatically or upon manual activation) adjusted until all the required markers are visible. A manual activation ensures that the camera does not perform sudden and unexpected movements. In general, the description given for the camera is applicable in analogy to any other tracking device, such as an EM transmitter.

The method in accordance with the invention is in particular a data processing method. The data processing method is preferably performed using technical means, in particular a computer. In particular, the data processing method is executed by or on the computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" also encompasses a cloud computer, in particular a cloud server. The term "cloud computer" also encompasses a cloud computer system which in particular comprises a system of at least one cloud computer, in particular a plurality of operatively interconnected cloud computers such as a server farm. The cloud computer is preferably connected to a wide area network such as the world wide web (WWW). Such a cloud computer is located in a so-called cloud of computers which are all connected to the world wide web. Such an infrastructure is used for "cloud computing" which describes computation, software, data access and storage services which do not require the end user to know the physical location and configuration of the computer which delivers a specific service. In particular, the term "cloud" is used as a metaphor for the internet (world wide web). The cloud in particular provides computing infrastructure as a service (IaaS). The cloud computer may function as a virtual host for an operating system and/or data processing application which is used for executing the method of the invention. The cloud computer is preferably an Elastic Compute Cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

The invention also relates to a program which, when running on a computer or when loaded onto a computer, causes the computer to perform one or more of all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit (CPU)) which executes the computer program elements and optionally a volatile memory (in particular, a random access memory (RAM)) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The present invention also relates to a tracking system for tracking trackable objects using a camera during a medical workflow comprising a plurality of workflow steps, wherein each trackable object has at least one marker. The tracking system comprises a tracking camera and a control unit. The control unit is adapted to acquire a set of camera positions, each of which is associated with at least one workflow step, in order to identify a workflow, sequentially and automatically move the camera to the camera positions associated with the workflow steps, and perform tracking only when the camera is in a fixed position.

In general, the control unit is adapted to carry out or initiate the method steps as explained above.

The present invention shall now be explained in more detail with reference to the accompanying figures. These figures show.

Figure 1:
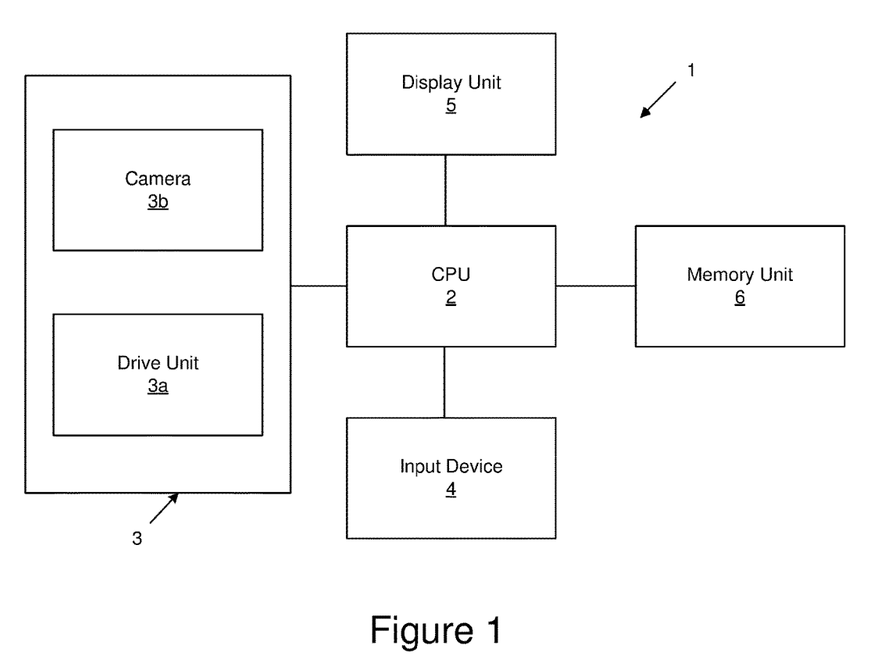
FIG. 1 a schematic structure of a medical tracking system.

FIG. 1 schematically shows the structure of a medical tracking system 1. The tracking system 1 comprises a CPU (central processing unit) 2 connected to an image pick-up unit 3, an input device 4, a display unit 5 and a memory unit 6. The image pick-up unit 3 comprises a base (not shown), a drive unit 3*a* and a camera 3*b*. The base of the image pick-up unit 3 is placed at a fixed position. The drive unit 3*a* is configured to drive the camera 3*b* relative to the base of the image pick-up unit 3, such that the camera 3*b* can assume a plurality of positions. The drive unit 3*a* could include a robotic arm.

The CPU 2 is configured to support a medical workflow comprising a plurality of workflow steps by enabling trackable objects to be tracked. To this end, the memory unit 6 stores a set of camera positions, wherein each camera position is associated with at least one workflow step. More than one workflow step can be associated with a particular camera position.

Depending on the workflow step, the CPU 2 determines a camera position from the set of camera positions in the memory unit 6 which corresponds to the workflow step and instructs the drive unit 3*a* of the image pick-up unit 3 to move the camera 3*b* to the determined camera position. Alternatively, the CPU 2 provides a control signal to the drive unit 3*a* which activates the drive unit 3*a* as required.

The CPU 2 is also configured to interpret the output signal of the camera 3*b* in order to detect the positions of markers within the field of view, also referred to as the tracking volume, of the camera 3*b*. When a plurality of markers, preferably three or four markers, are attached to an object in a known configuration, the position of the object can be calculated from the positions of its markers. The CPU 2 can thus track objects. The positions of the tracked objects could be displayed on the display unit 5 and/or used in a medical navigation process.

In order to determine the camera position to be set, the CPU 2 needs to know the workflow and the workflow step. Information regarding the workflow and the workflow step can be inputted using the input device 4, which can be a touch-sensitive surface of the display unit 5 or any other suitable input means. Alternatively, the CPU 2 can determine the objects present in the operating room by analysing the output signal of the camera 3*b* (or any other camera) and then determine the workflow from the set of objects present. For this purpose, the memory unit 6 can store a set of workflows and lists of objects to be used in each workflow. From the current positions of the objects, the CPU 2 can also determine the current workflow step and accordingly the associated camera position. The workflow step, in particular the transition from one workflow step to the next, can also be determined by the CPU 2 by analysing the output signal of the camera 3*b* (or any other camera) and detecting a gesture which is performed by a person such as a surgeon and indicates to the tracking system 1 that the next workflow step is to be performed or indicates which workflow step is to be performed next.

Figure 2:
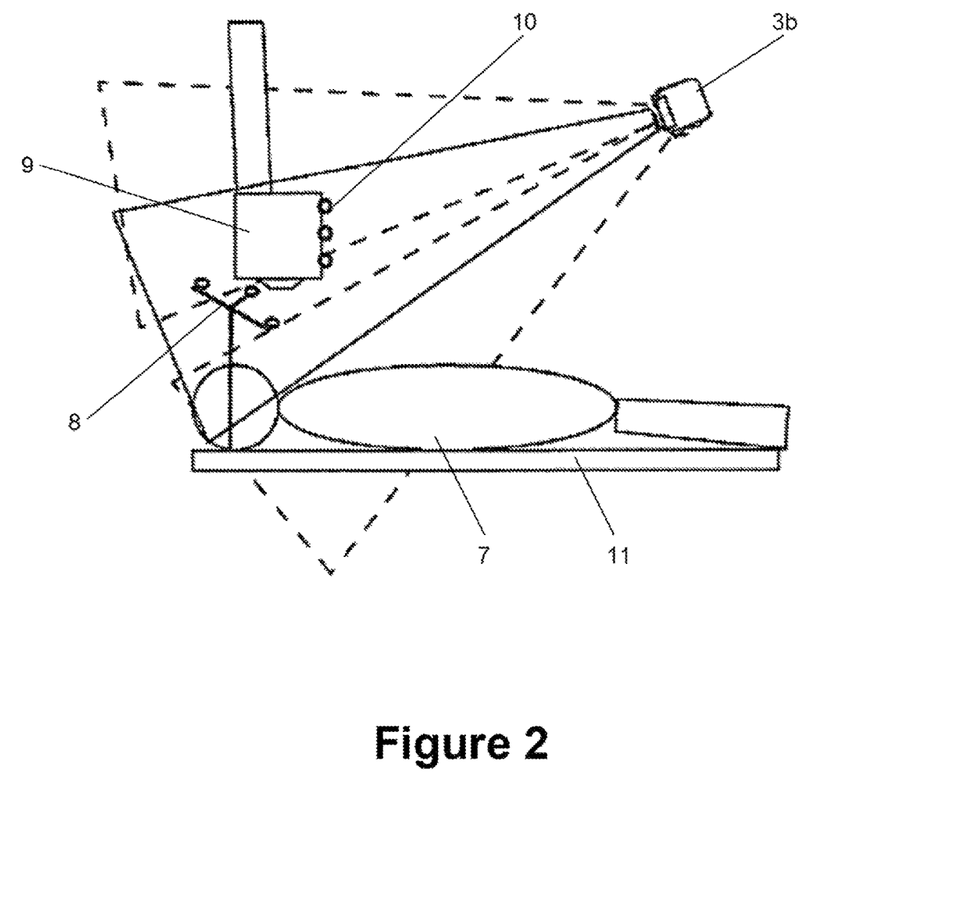
FIG. 2 an example operating room configuration.

FIG. 2 schematically shows a scenario corresponding to one step of a medical workflow. In this scenario, a patient 7 is lying on an operating room table 11. In the corresponding workflow step, an x-ray image of the patient 7, in particular of the patient's head, is to be acquired using an x-ray imaging unit 9. In order to analyse the x-ray image, it is essential to know the viewing direction from which the image was recorded. To this end, a marker device 8 comprising three markers in a known configuration is rigidly attached to the patient 7, in particular to the patient's head. A marker device 10 comprising three markers in a known configuration is attached rigidly to the x-ray imaging unit 9. If the relative position between the marker devices 8 and 10, and therefore between the patient 7 and the x-ray imaging unit 9, is known, then the viewing direction of an x-ray image of the patient 7 generated by the x-ray imaging unit 9 is also known. It is thus advantageous to track the trackable objects, i.e. the patient 7 and the x-ray imaging unit 9 using the medical tracking system 1.

In order to track the patient 7 and the x-ray imaging unit 9, the marker devices 8 and 10 need to be within the tracking volume of the tracking camera 3*b*. The camera 3*b* therefore needs to be placed in a position in which this requirement is fulfilled. As explained above, the camera 3b is automatically moved to such a position, which belongs to a set of camera positions and is associated with a workflow step according to the scenario shown in FIG. 2. How this camera position is determined and stored in the set of camera positions will now be described with reference to this figure.

In FIG. 2, the tracking volume of the camera 3b is indicated as a conical region. In order to determine the camera position, the camera 3b is moved into three test positions, wherein the tracking volumes for the first and third test position are indicated by a dashed boundary line and the tracking volume for the second test position is indicated by a continuous boundary line. The first test position corresponds to the upper tracking volume, while the third test position corresponds to the lower tracking volume.

A set of candidate positions is determined from the set of test positions. A test position is added to the set of candidate positions if all the markers of all the objects to be tracked in the corresponding workflow step are within the tracking volume of the camera 3b when the camera 3b is in said test position. In the present example, if the camera 3b is in the first test position or in the third test position, the markers of the marker devices 8 and 10 do not all lie within the tracking volume. The first and third test positions are therefore not added to the set of candidate positions. In the second test position, the markers of the marker devices 8 and 10 all lie within the tracking volume of the camera 3b, such that the second test position is added to the set of candidate positions.

In the present case, after all the test positions have been tested, the set of candidate positions only comprises one camera position, i.e. the second test position. This camera position is thus added to the set of camera positions and associated with the workflow step. If the set of candidate positions comprises more than one camera position, one or more suitable criteria are applied in order to select one candidate position as the camera position to be added to the set of camera positions.

When the medical workflow is performed, one workflow step corresponds to the scenario shown in FIG. 2. When this workflow step is reached, the camera position associated with this workflow step is determined from the set of camera positions, and the camera 3b is automatically moved into this camera position. The patient 7 and the x-ray imaging unit 9 are only tracked once the camera 3b has reached the determined camera position and are not tracked while the camera is moving.

Figure 3:
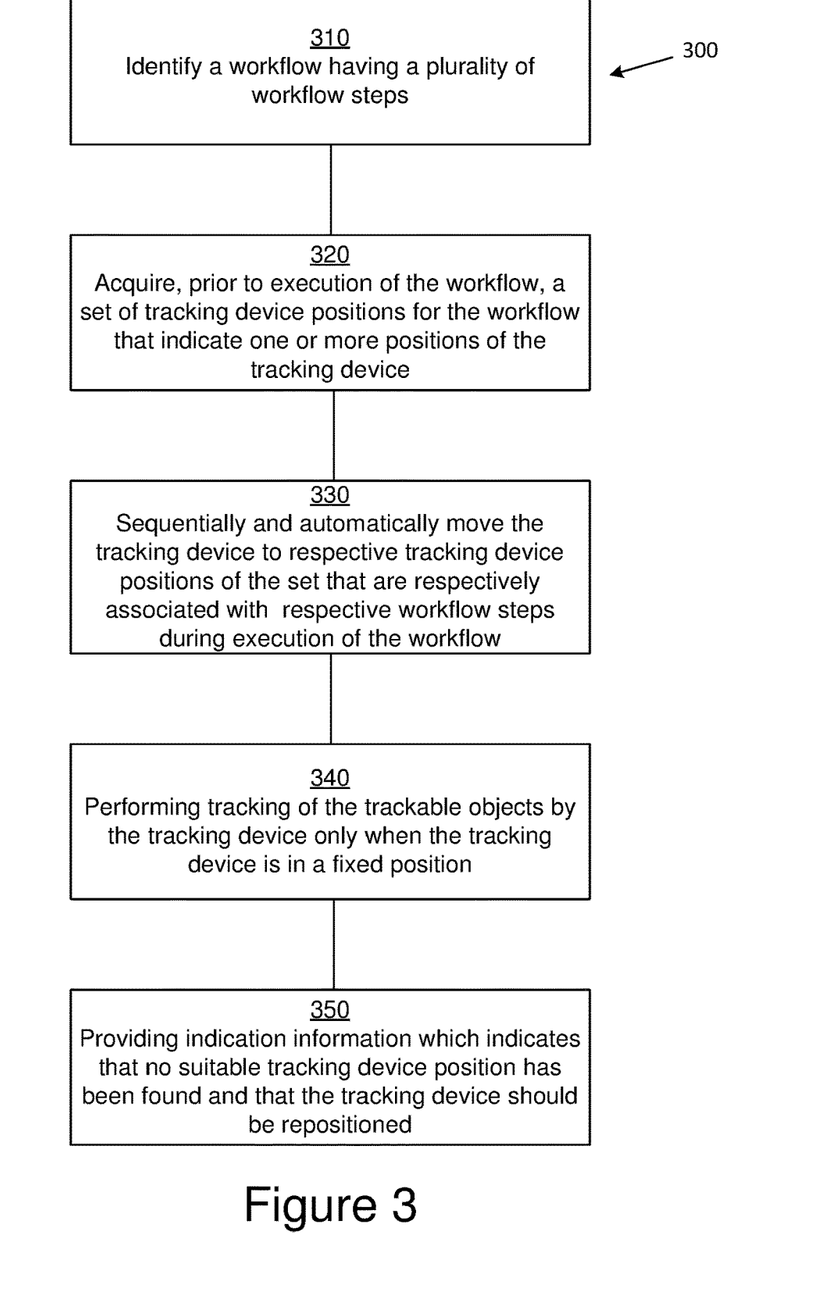
FIG. 3 an example embodiment of a method for tracking trackable objects using a medical tracking device.

FIG. 3 illustrates an example embodiment of a method 300 for tracking trackable objects using a medical tracking device, as described above.

At step 310, a workflow having a plurality of workflow steps is identified.

At step 320, prior to execution of the workflow, a set of tracking device positions for the workflow that indicate one or more positions of the tracking device is acquired. Each tracking device position of the set is associated with at least one workflow step of the workflow.

At step 330, the tracking device is sequentially and automatically moved to respective tracking device positions of the set that are respectively associated with respective workflow steps during execution of the workflow. The moving of the tracking device is responsive to acquired input indicating transitions between workflow steps.

At step 340, tracking of the trackable objects by the tracking device is performed only when the tracking device is in a fixed position.

At step 350, indication information which indicates that no suitable tracking device position has been found and that the tracking device should be repositioned is provided.

It should be noted that the tracking method described herein does not relate to or comprise any surgical step. In particular, attaching a marker or marker device to a (human) body is not a part of the present invention. The present invention is based on a state in which a marker or marker device has already, i.e. previously, been attached. This invention relates solely to tracking trackable objects, positioning the camera of a tracking system and determining a camera position to be associated with at least one workflow step.

It is claimed:

1. A method for tracking trackable objects using a medical tracking device, the tracking device being a tracking camera or an EM transmitter, during a medical workflow comprising a plurality of workflow steps, wherein each trackable object has at least one marker and the method comprises the steps of:
   identifying a workflow having a plurality of workflow steps;
   acquiring, prior to execution of the workflow, a set of tracking device positions for the workflow that indicate one or more positions of the tracking device, wherein each tracking device position of the set is associated with at least one workflow step of the workflow;
   sequentially and automatically moving the tracking device to respective tracking device positions of the set that are respectively associated with respective workflow steps during execution of the workflow, wherein moving the tracking device is responsive to acquired input indicating transitions between workflow steps; and
   performing tracking of the trackable objects by the tracking device only when the tracking device is in a fixed position.

2. The method according to claim 1, wherein the tracking device covers a tracking volume in each position, and a position for inclusion in the set of tracking device positions is determined automatically by:
   sequentially moving the tracking device to a plurality of test positions;
   storing a test position as a candidate position if all the markers of all the trackable objects used within a particular workflow step are within the tracking volume of the tracking device; and
   selecting the candidate position in which the distances from the markers to the centre of the tracking volume are minimised as a position to be included in the set of tracking device positions.

3. The method according to claim 2, wherein the highest possible candidate position is selected.

4. The method according to claim 2, wherein if the tracking device is a camera, the candidate position in which the angles between the line of sight of the camera and normal vectors which are normal to a plane in which the markers of a trackable object lie are minimised.

5. The method according to claim 2, wherein a test position is stored as a candidate position if all the markers of all the trackable objects used within a particular workflow step are within a predetermined sub-volume of the tracking volume.

6. The method according to claim 2, wherein priorities are assigned to the trackable objects used within a particular workflow step, and a test position is stored as a candidate position if all the markers of objects with a priority which is higher than a threshold value are within a predetermined sub-volume of the tracking volume.

7. The method according to claim 2, further comprising the step of providing indication information which indicates that no suitable tracking device position has been found and that the tracking device should be repositioned.

8. The method according claim 1, wherein the workflow is identified automatically.

9. The method according to claim 8, wherein the workflow is identified by identifying trackable objects used in the workflow.

10. The method according claim 1, wherein a tracking device position is corrected on the basis of the position of a marker attached to a boxy or to a part of a body to be treated.

11. The method according to claim 1, wherein a position is entered into the set of tracking device positions manually.

12. The method according to claim 1, wherein the tracking device position is corrected on the basis of the detectability of the markers.

13. The method according to claim 1, further comprising acquiring a user input indicating a transition between workflow steps.

14. The method according to claim 13, wherein the user input is a user gesture captured by the tracking device.

15. The method according to claim 1, further comprising determining a workflow step based on an arrangement of trackable objects determined by the tracking device.

16. The method according to claim 1, further comprising disabling tracking by the tracking device while the tracking device is moving between tracking device positions from the set.

17. A non-transitory computer-readable storage medium having stored thereon computer-executable instructions for a computer program which, when running on a computer or when loaded onto a computer, causes the computer to:
  identify a workflow having a plurality of workflow steps;
  acquire, prior to execution of the workflow, a set of tracking device positions for the workflow that indicate one or more positions of the tracking device, wherein each tracking device position of the set is associated with at least one workflow step of the workflow;
  sequentially and automatically move the tracking device to respective tracking device positions of the set that are respectively associated with respective workflow steps during execution of the workflow in response to acquired input indicating transitions between workflow steps; and
  performing tracking of the trackable objects by the tracking device only when the tracking device is in a fixed position.

18. A tracking system for tracking trackable objects having markers during a medical workflow, said system comprising a tracking device being a tracking camera or an EM transmitter and a computer configured to:
  identify a workflow having a plurality of workflow steps;
  acquire, prior to execution of the workflow, a set of tracking device positions for the workflow that indicate one or more positions of the tracking device, wherein each tracking device position of the set is associated with at least one workflow step of the workflow;
  sequentially and automatically move the tracking device to respective tracking device positions of the set that are respectively associated with respective workflow steps during execution of the workflow in response to acquired input indicating transitions between workflow steps; and
  perform tracking of the trackable objects by the tracking device only when the tracking device is in a fixed position corresponding to one of the tracking device positions of the set.

\* \* \* \* \*